United States Patent

Cochran et al.

[11] Patent Number: 6,122,048
[45] Date of Patent: *Sep. 19, 2000

[54] INTEGRAL FIELD LENS ILLUMINATION FOR VIDEO INSPECTION

[75] Inventors: Don W. Cochran, Gates Mills; Steve Cech, Aurora; Terry L. Graves, Wadsworth; Howard Fein, Richmond Heights, all of Ohio

[73] Assignee: Pressco Technology Inc., Solon, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/819,304

[22] Filed: Mar. 18, 1997

Related U.S. Application Data

[63] Continuation-in-part of application No. 08/296,688, Aug. 26, 1994, abandoned.
[51] Int. Cl.[7] .................................................. G01N 21/00
[52] U.S. Cl. ................................... 356/239.4; 356/240.1; 250/223 B; 348/127; 382/142
[58] Field of Search ................................... 356/394, 237, 356/239, 240, 240.1, 239.4, 239.5, 239.6, 237.1; 348/126, 87, 127; 250/562, 572, 223 B; 382/151, 142

[56] References Cited

U.S. PATENT DOCUMENTS

| | | |
|---|---|---|
| 2,466,161 | 4/1949 | Doll . |
| 2,798,605 | 7/1957 | Richards . |
| 3,107,011 | 10/1963 | Mathias et al. . |
| 3,171,033 | 2/1965 | Mathias et al. . |
| 3,711,722 | 1/1973 | Kavanagh . |
| 3,857,637 | 12/1974 | Obenreder . |
| 3,886,356 | 5/1975 | Gomm et al. . |
| 3,894,806 | 7/1975 | Remy et al. . |
| 4,026,656 | 5/1977 | Kusz et al. . |
| 4,145,714 | 3/1979 | MacDonald et al. ............... 356/241 |
| 4,280,624 | 7/1981 | Ford . |
| 4,284,353 | 8/1981 | Yoshida et al. . |

(List continued on next page.)

Primary Examiner—Hoa Q. Pham
Attorney, Agent, or Firm—Fay, Sharpe, Fagan, Minnich & McKee

[57] ABSTRACT

A video inspection system is provided wherein light from a light source is directed through a field lens. The field lens directs the incident light first in the direction of an object under inspection and then, after reflecting from said object, redirecting the reflected light toward the aperture of an imaging lens/camera assembly. This redirection technique results in magnification of selected regions of the object.

34 Claims, 7 Drawing Sheets

U.S. PATENT DOCUMENTS

| | | |
|---|---|---|
| 4,330,205 | 5/1982 | Murakami et al. . |
| 4,376,951 | 3/1983 | Miyazawa . |
| 4,378,159 | 3/1983 | Galbraith . |
| 4,391,373 | 7/1983 | Wiggins . |
| 4,424,441 | 1/1984 | Bieringer et al. . |
| 4,428,674 | 1/1984 | Giebel et al. . |
| 4,435,641 | 3/1984 | Hajime . |
| 4,459,023 | 7/1984 | Reich et al. . |
| 4,506,980 | 3/1985 | Pryor et al. . |
| 4,511,222 | 4/1985 | Biren . |
| 4,538,909 | 9/1985 | Bible et al. . |
| 4,560,273 | 12/1985 | Ando et al. . |
| 4,583,854 | 4/1986 | Lozar . |
| 4,606,635 | 8/1986 | Miyazawa et al. . |
| 4,626,079 | 12/1986 | Nakamura et al. . |
| 4,644,151 | 2/1987 | Juvinall ................................ 250/223 B |
| 4,650,326 | 3/1987 | Nagamine et al. . |
| 4,682,023 | 7/1987 | Yoshida . |
| 4,691,231 | 9/1987 | Fitzmorris et al. . |
| 4,692,690 | 9/1987 | Hara et al. ................................ 356/394 |
| 4,758,084 | 7/1988 | Tokumi et al. . |
| 4,760,270 | 7/1988 | Miller . |
| 4,779,967 | 10/1988 | Murphy et al. ........................ 350/518 |
| 4,865,447 | 9/1989 | Shay . |
| 4,871,257 | 10/1989 | Suzuki et al. . |
| 4,912,318 | 3/1990 | Kajiura et al. . |
| 4,914,289 | 4/1990 | Nguyen et al. . |
| 4,924,107 | 5/1990 | Tucker . |
| 4,927,254 | 5/1990 | Kino et al. ................................ 350/507 |
| 4,965,454 | 10/1990 | Yamauchi et al. . |
| 5,030,008 | 7/1991 | Scott et al. ................................ 356/394 |
| 5,030,823 | 7/1991 | Obdeijn . |
| 5,051,825 | 9/1991 | Cochran et al. ........................ 356/237 |
| 5,072,127 | 12/1991 | Cochran et al. ........................ 356/240 |
| 5,095,204 | 3/1992 | Novini . |
| 5,142,416 | 8/1992 | Nakamura et al. . |
| 5,216,481 | 6/1993 | Minato . |
| 5,220,400 | 6/1993 | Anderson et al. . |
| 5,249,034 | 9/1993 | Minato . |
| 5,365,084 | 11/1994 | Cochran et al. ........................ 356/430 |
| 5,365,341 | 11/1994 | Sugawara ................................ 356/394 |
| 5,451,773 | 9/1995 | Triner et al. . |
| 5,519,496 | 5/1996 | Borgert et al. ........................ 356/237 |
| 5,563,736 | 10/1996 | Lewis ................................ 359/432 |
| 5,592,286 | 1/1997 | Fedor . |
| 5,699,152 | 12/1997 | Fedor et al. . |
| 5,805,279 | 9/1998 | Palombo et al. . |

INTEGRAL FIELD LENS ILLUMINATION FOR VIDEO INSPECTION

This application is a continuation-in-part application of U.S. Ser. No. 08/296,688 filed Aug. 26, 1994, abandoned.

BACKGROUND OF THE INVENTION

This application pertains to the art of video inspection, and more particularly to specialized illumination and image capture therefor. The invention is directed to inspection of discrete specimens, particularly those having regions of heightened interest to the user. Accordingly, the application will be described with specific reference thereto, although it will be appreciated that the invention has broader application in any video inspection environment for which acquisition of detailed images is desirable.

High-speed, automated inspection of mass-produced articles is rapidly becoming an essential part of industrial production. As increasing reliance is placed on automated video inspection, increasing capability and resolution is also desired.

A first generation of improvement to the video inspection system was associated with improvements to basic inspection algorithms. A subsequent generation of improvement was directed toward improving the actual image captured. Such systems employed such components as a solid-state LED array, optionally coupled with a diffuser, to obtain more homogeneous lighting. Of course, the more uniform an illumination field, the more accurate a resultant, captured image would be.

An existing concern with state-of-the-art video inspection systems is competing objectives of analysis. More particularly, an overall analysis of an image is often desirable. However, detailed analysis of a sub-portion, or region, of the specimen or object is also advantageous. This latter advantage is particularly necessary for specimens having a high stress area or the like.

The need to provide a detailed analysis of a sub-portion of the image while maintaining global inspection of the inspected object can, in some instances, manifest itself as a critical machine vision inspection limitation. The limitations of current state-of-the-art machine vision systems become particularly apparent when a detailed inspection of a thin annular region located away from the object center is required. This situation often arises within the container industry wherein a fairly thin annular region located away from an object center is dedicated as a sealing surface for multi-piece containers. Product failure often occurs when this seal surface is compromised during construction of the container. For this reason, detailed inspection of this critical area of the object is a quality control requirement. However, the spatially-distributed nature of this critical area of interest does not lend itself to a detailed yet efficient machine vision inspection using state-of-the-art techniques. To obtain sufficient spatial resolution to discern defects of interest, several camera/imaging lens assemblies can be targeted along the annular region of interest, each focused to produce a magnified image of a unique portion of the object under inspection. In this fashion, a detailed analysis of the complete object can be synthesized. However, the requirement for multiple imaging lens/camera assemblies significantly impacts the cost of the machine vision solution. When a more economical single imaging lens/camera solution is pursued, detailed spatial resolution of the critical seal surface is sacrificed.

In short, the combination of standard imaging lens components and a generally rectangular array of sensor pixels does not efficiently sample thin annular regions which happen to be located away from the center of the object under inspection. When limited to using this inspection technique, the majority of the sensor pixels end up sampling non-critical regions of the part. Only a limited number of pixels are used to inspect the critical area of interest. This results in limited inspection resolution where it is required.

The subject invention addresses the above concerns as well as others and provides an efficient mechanism for completing detailed video inspection on limited annular regions of generally circular objects using a single imaging lens/camera assembly video inspection system.

SUMMARY OF THE INVENTION

A video inspection system is provided wherein light from a light source is directed through a field lens. The field lens directs the incident light first in the direction of an object under inspection and then, after reflecting from said object, redirecting the reflected light toward the aperture of an imaging lens/camera assembly.

In one aspect of the invention, the field lens is used to impart some degree of radially dependent magnification to the imaged field.

In another aspect of the invention, the field lens comprises one of a spherical refractive, a spherical reflective, an aspherical refractive, an aspherical reflective, a diffractive, a planar or axicon, or a gradient index refractive optical element.

In another aspect of the invention, the field lens operates in a generally transmissive mode.

In another aspect of the invention, the field lens operates in a generally reflective mode.

In another aspect of the invention, a video inspection method is provided.

BRIEF DESCRIPTION OF THE DRAWINGS

The invention may take form in certain parts, and arrangements of parts, as will be provided in the specification and illustrated in drawings which form a part hereof and wherein.

DETAILED DESCRIPTION OF THE PREFERRED EMBODIMENT

Figure 1:
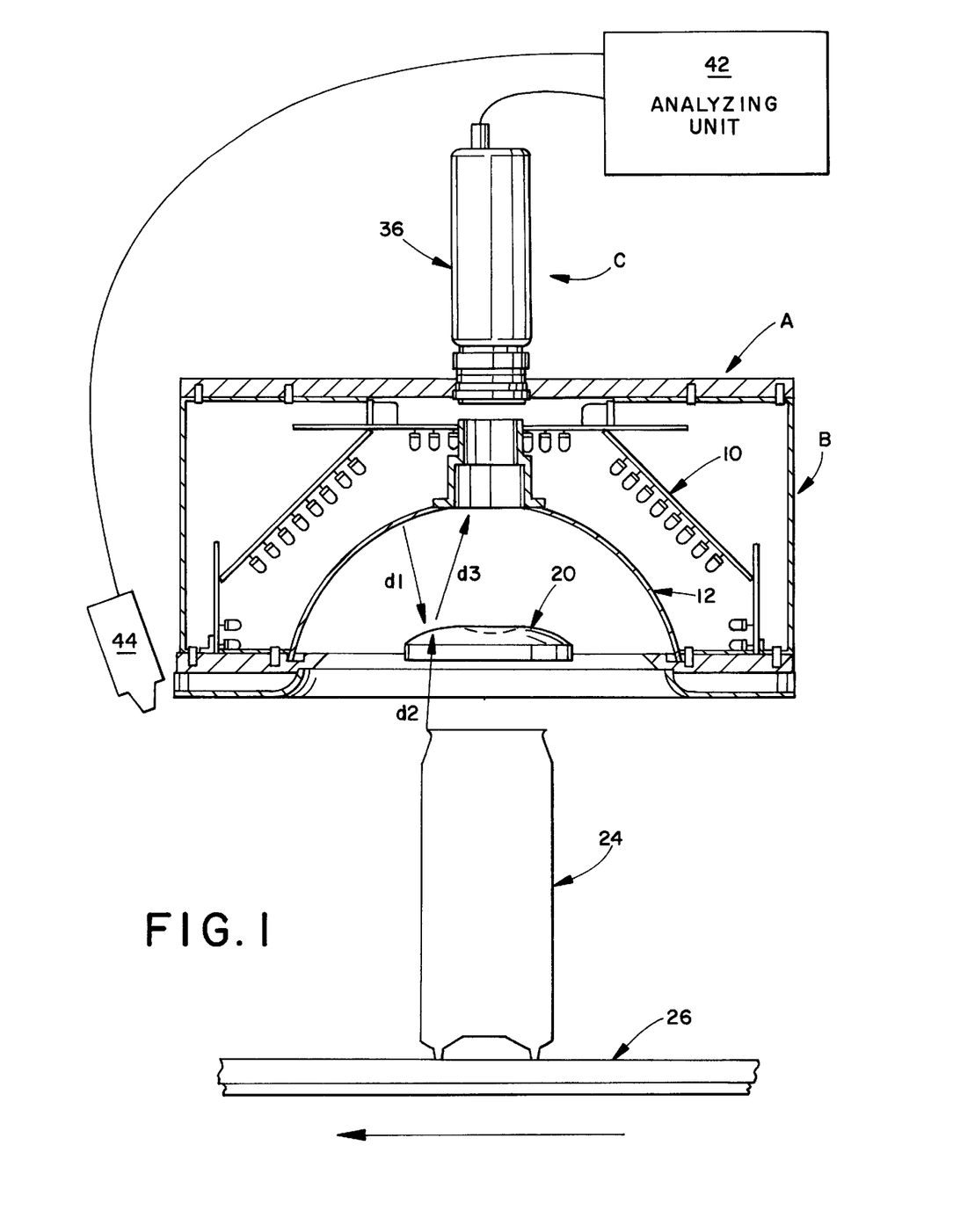
FIG. 1 illustrates the overall inspection illumination and image capture system of the subject invention.

Turning now to the drawings wherein the figures are for the purpose of illustrating the preferred embodiment only, and not for the purpose of limiting the same, FIG. 1 illustrates an automated video inspection system A which includes an illumination subsystem B and an image acquisition subsystem C. The disclosed system facilitates enhanced defect detection and optical inspection and is particularly suited for discrete parts, as is used in the container industry. For example, the system may be used to inspect manufactured food or beverage containers. In addition, the system may be used to inspect manufactured durable goods.

The system is used to particular advantage at high speed—where typically only one opportunity exists to obtain an image—to facilitate inspection of a large number of specimens in a relatively short period of time. The system, though, will operate effectively at any speed.

A suitable light source is formed, or fabriciated, by a solid-state illumination source, such as a pulsed array of light emitting diodes, or elements. However, any source of sufficient illumination levels may be implemented.

For example, the preferred strobed light, which includes the noted LED array, inert gas strobes, and the like, maintains an advantage of "freezing" moving specimens so that an image may be obtained. In such a mode, the pulsed light source is used to stop the action of a dynamic object. However, continuous light sources such as halogen light sources or solid state light sources operated in a continuous forward current manner, or mode, may be used and require the addition of a commonly-available electronic or mechanical shutter mechanisms to "freeze" a captured image. A multi-spectrum light source is also advantageously provided in certain applications. In addition, the camera could also be electrically strobed to stop the action of a dynamic object in obtaining an image.

The system allows for optically magnifying an image portion while utilizing normal camera optics to acquire discrete images. Resultant information on defects generated is made available for subsequent analysis and comparison.

In the structure of FIG. 1, a light source 10 is used to generate light generally in a direction d1. In the preferred embodiment, the light source 10 is advantageously programmable so as to selectively generate light. Light from the light source 10 is passed through a diffuser 12 to increase homogeneity thereof.

The diffuser 12 is advantageously comprised of a translucent or transparent material, such as glass or plastic. The surface is optically "rough" in such a way that incident light will transmit through the medium and be modified so as to be uniformly distributed over some area as diffused, transmissively scattered light. The particular properties of the diffusion are highly application specific. Selection may be made by choice of translucence, transparency, and roughness.

Light from the light source 10 which has passed through the diffuser 12 propagates along direction $d_1$. This light is then communicated to a field lens 20. In the preferred embodiment, the field lens comprises a refractive aspheric optical element.

The specimen illumination may also be directed through other modifying optical elements. Such modifying elements are suitably beam splitters, mirrors, lenses, or the like. Such optical elements may be disposed either prior to or following the field lens, as defined from the light source 10, to the specimen 24.

After passing through the field lens, the light reflects off the part, specimen, or object, 24 under inspection which is propagated to a viewing area via conveyor 26. The conveyor 26 is preferably comprised of a moving belt or the like that preferably operates at high speed to facilitate high speed, automated inspection of objects.

A portion of the reflected light travels in the general direction d2 back toward the field lens 20. At the field lens 20, the reflected rays are redirected in a direction d3 to the open aperture of a standard imaging lens/camera assembly 36.

Figure 2:
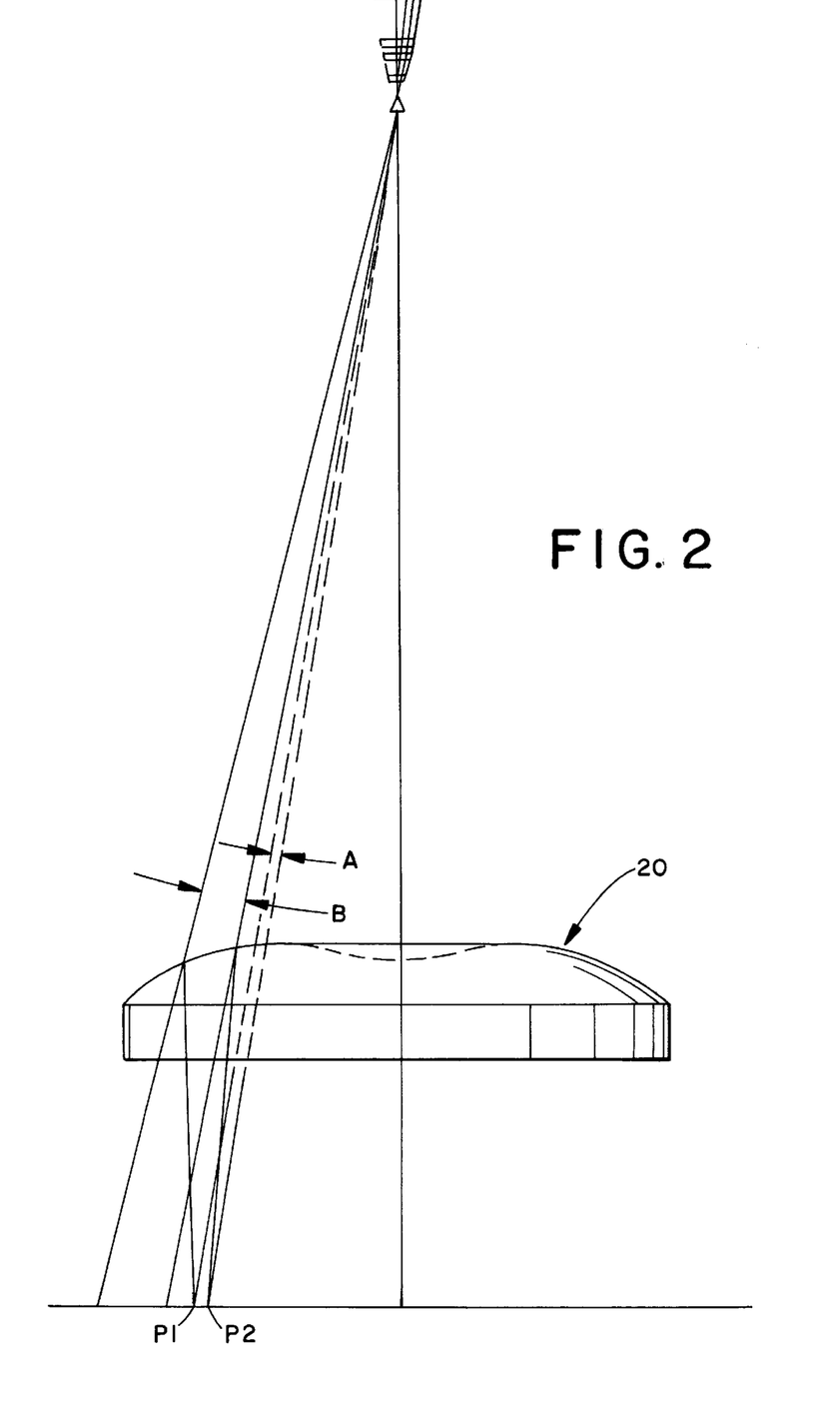
FIG. 2 illustrates an example of a field lens imparting a selective degree of magnification.

This redirection behavior is generally illustrated in FIG. 2 wherein an aspheric refractive optical element 20 is used to magnify the angular separation between two points P1 and P2 located in the same plane within the annular region of interest. As shown, a properly designed and situated field lens 20 imparts some degree of selective annular magnification. In this example, the properties of the field lens 20 act to bend the reflected light rays emanating from the part under inspection in a manner which amplifies the apparent separation distance between the two points P1 and P2 located within the annular zone of interest. The degree of amplification or magnification is evident by comparing the angle subtended by the two points of interest in a standard imaging view (indicated by angle A) with the angle subtended after passing through the field lens (indicated by angle B).

As those skilled in the art will recognize, this angular separation is linearly mapped to a spatial separation, when implemented in the context of the present invention, by the imaging lens/camera assembly 36. The camera receives the redirected light in a linear fashion and maps the modified radiation fields representing the redirected light onto a surface of a spatial light recording medium. Thus, a selected, or application specific, annular region of the object under inspection may be magnified or spatially remapped.

The system outlined in FIG. 2 shows a field lens component constructed using refractive aspheric lens design techniques. The lens may be operated in a generally transmissive mode or a generally reflective mode. A similar effect could also be achieved using aspherical reflective, spherical refractive, spherical reflective, planar or axicon, diffractive, or gradient index refractive optical elements operated in either a generally transmissive mode or a generally reflective mode. It should be recognized that all of these specific techniques and materials, as well as others obvious to those in the field, are within the scope of the present invention.

Figure 3:
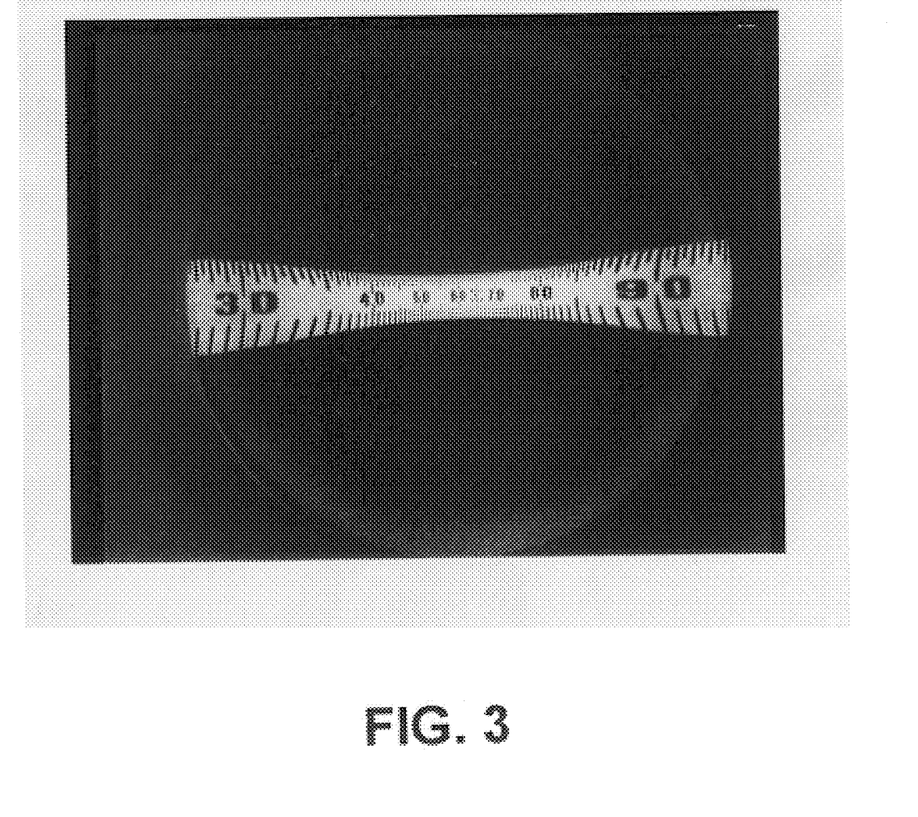
FIG. 3 is an exemplary photograph of a portion of a tape measure viewed through a field lens using the image acquisition technique according to the present invention.
Figure 4:
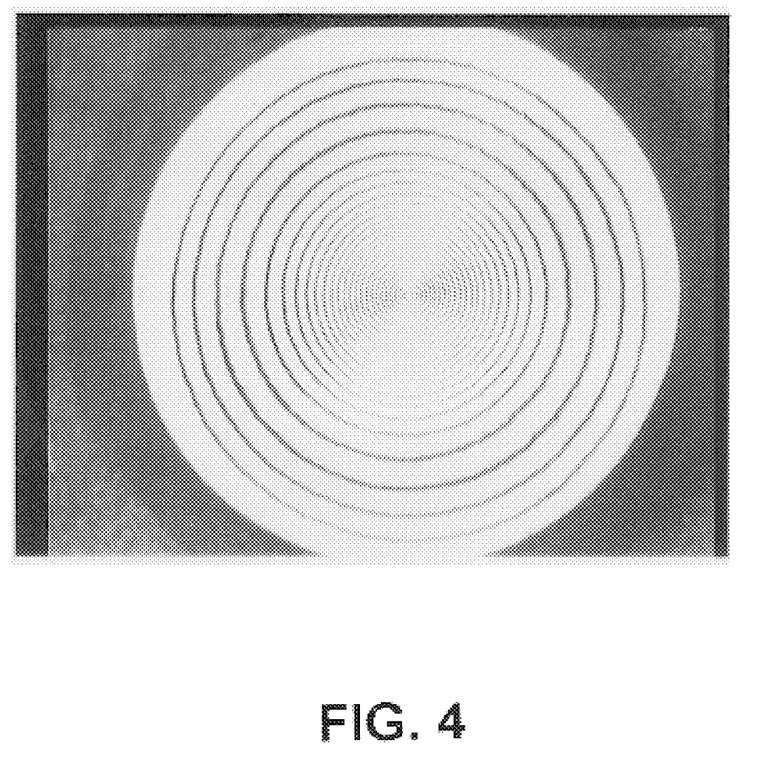
FIG. 4 is an exemplary photograph of a pattern of concentric circles viewed through a field lens using the image acquisition technique according to the present invention.
Figure 5:
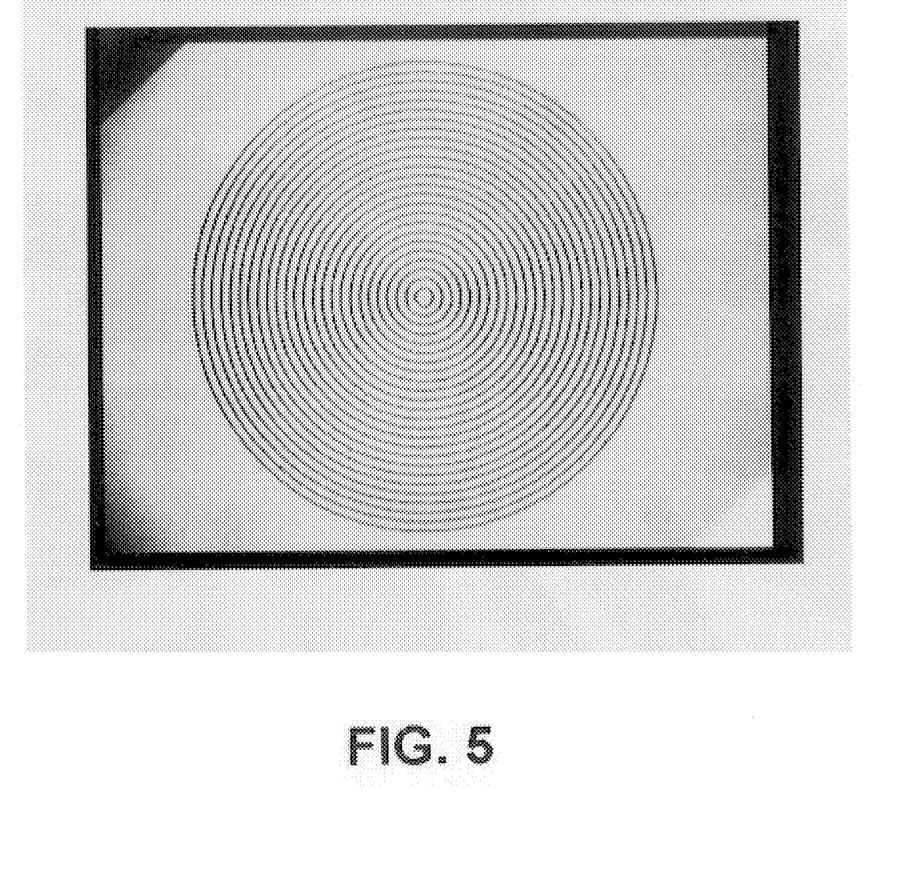
FIG. 5 is the pattern of concentric circles shown in FIG. 4 when viewed using standard imaging techniques.

To further illustrate the effect of use of a field lens, FIG. 3 is a photograph of a ruled object acquired using a novel image acquisition technique as described by this invention. Likewise, FIG. 4 is a photograph of another test object. In the case of FIG. 4, the test object consists of a number of equally spaced concentric rings. A standard imaging view, without use of a field lens, of the same test pattern is given in FIG. 5.

Figure 6:
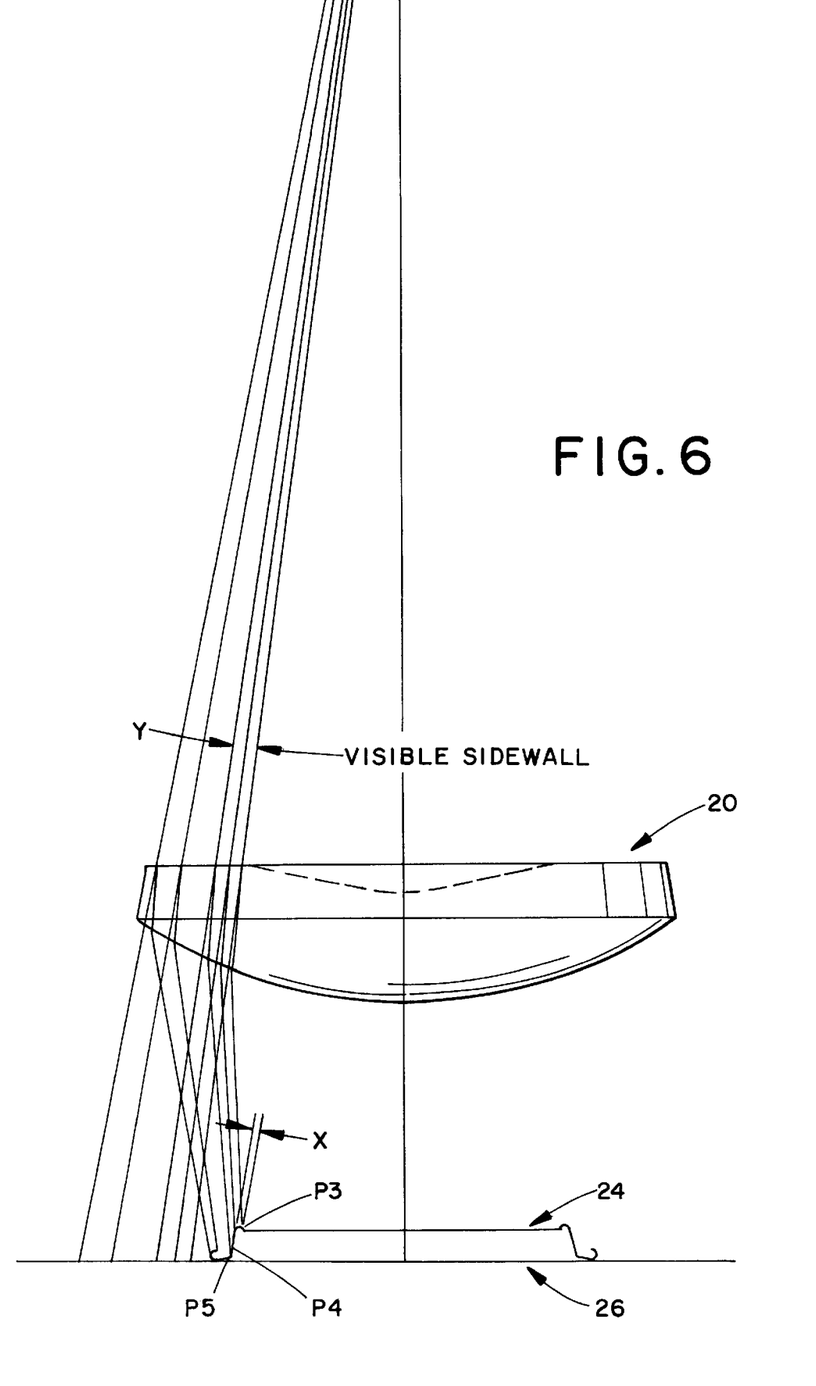
FIG. 6 is a representation of light rays propagated through a field lens onto a discrete object using the image acquisition technique of the present invention; and, FIG. 7 shows the method according to the present invention.

With reference to FIG. 6, a similar optical front-end technique using a lens 20 of a different shape than that of FIG. 2 can be applied to the particular application of interest here. That is, the technique is preferably used to spatially remap selected regions of interest to achieve a more advantageous view or look angle to points or regions located on the surface of the part 24 under inspection. A more advantageous view of multiple regions is thus achieved. In this case, points P3, P4 and P5, located on the outside wall of a cylindrical container in the field of view of the camera 36, become more clearly visible using the preferred image acquisition system because the angle X subtended by the point P3 and P5 (as well as the respective angles between points P3 and P4 and point P4 and P5) in a standard imaging view is amplified, or increased, after refraction through the field lens 20. For example, the angle subtended by the points P3 and P5 is amplified to an angle Y. Without the presence of the modifying field lens 20, the points P3, P4 and P5 would be obscured from the field-of-view of camera 36 and therefore unavailable for inspection operations.

With this architecture, the field lens 20 provides for pre-enlargement of an image prior to using integral camera optics disposed within the camera 36 to form a generated image. It is to be appreciated that the lens shown in FIG. 6, as well as other suitably shaped lenses, can be used to replace the lens 20 shown in FIGS. 1 and 2 depending on the needs of the user.

Referring back now to FIG. 1, the camera 36 is suitably comprised of solid-state, charge-coupled device ("CCD"). Digitized images captured therefrom are communicated via any suitable interface to any suitable image analyzing unit 42 which are commercially available and within the understanding of one of ordinary skill in the art.

In the image analyzing unit 42, captured images, once analyzed, are then compared to stored images, or other preselected criteria, to facilitate selective rejection of unacceptable specimens. When an unacceptable specimen is detected, a rejection mechanism, such as illustrated by an error blow-off unit 44, is enabled. When activated, a unit such as that of 44 will remove a defective specimen from the conveyor means 26.

Figure 7:
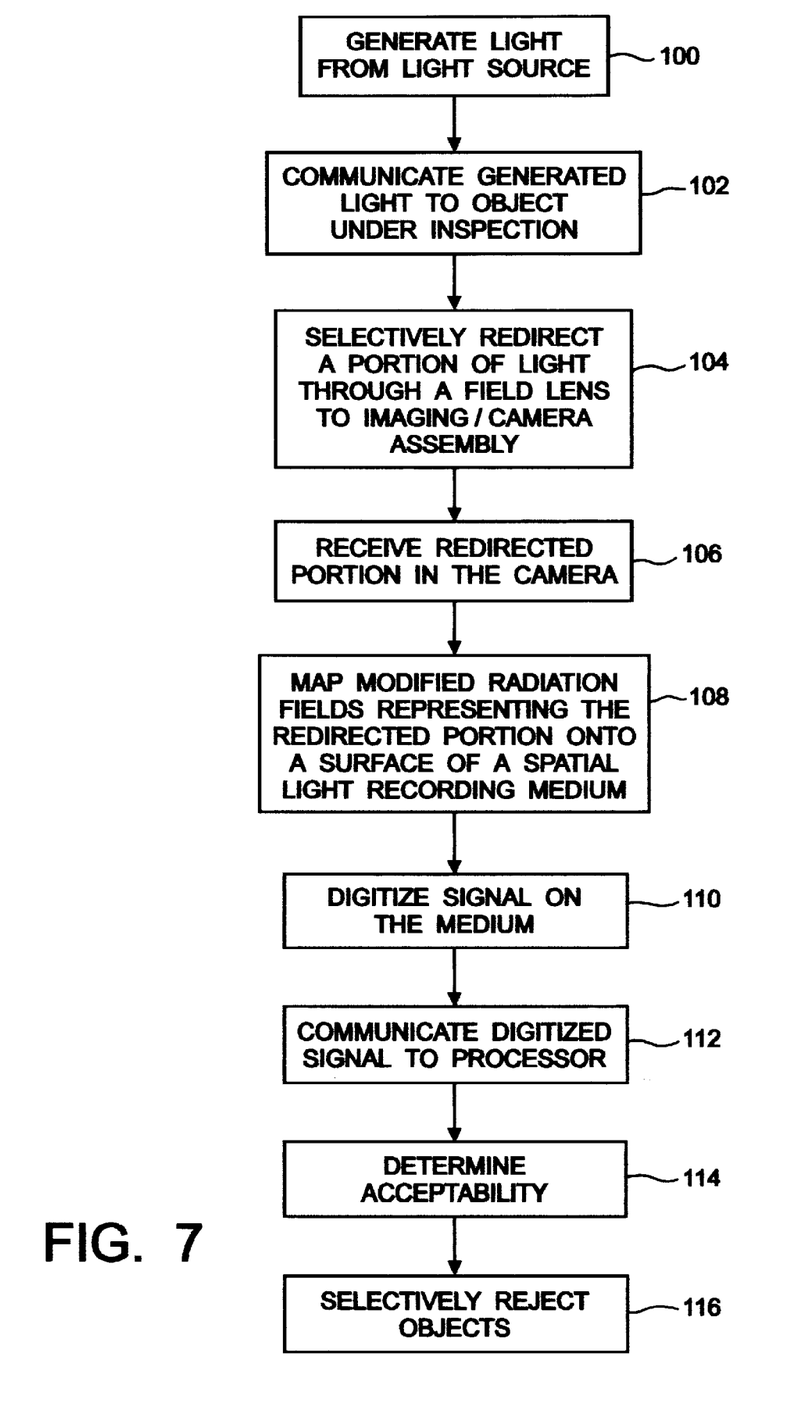

The method of the present invention is illustrated in FIG. 7. More specifically, the video inspection method comprises generating light from a light source (step 100), communicating generated light to an object under inspection (step 102), selectively redirecting a portion of the light through a field lens to an imaging lens/camera assembly to magnify or spatially remap a selected annular region of the object after reflection from the object under inspection (step 104), receiving the redirected portion in a linear fashion in the camera (step 106), and mapping modified radiation fields representing the redirected portion onto a surface of a spatial light recording medium (step 108).

The video inspection method may further comprise digitizing the signal present on the surface of the spatial light recording medium (step 110), communicating the digitized signal to a processing element (step 112), determining acceptability of the object under inspection from information contained within the digitized signal (step 114), and selectively rejecting an associated specimen in accordance with acceptability criteria as determined by the processing element (step 116).

This invention has been described with reference to a preferred embodiment. It is intended that any variations are included insofar as they come within the scope of the following claims or the equivalents thereof.

Having thus described the invention, it is now claimed:

1. A video inspection system comprising:
    a light source for generating light;
    a field lens for
        receiving a portion of the light emitted by the light source,
        communicating the light portion to an object under inspection,
        receiving the light portion after the light portion has reflected off the object under inspection, and
        selectively re-directing light rays which have reflected off of the object under inspection in a manner which results in a non-linear magnification of selected regions of interest on the object;
    an imaging lens/camera assembly adapted to receive light rays representing a modified image of the object under inspection, the modified image having the selected regions magnified in a non-linear manner.

2. The video inspection system as set forth in claim 1 further comprising:
    a processor;
    means for communicating digitized picture information from the camera to the processor;
    the processor including means for determining acceptability of the item under inspection from the digitized picture information; and,
    means for selectively rejecting an associated specimen in accordance with acceptability of the object under inspection as determined by the processor.

3. The video inspection system as set forth in claim 2 wherein the field lens component operates in one of a generally transmissive mode and a generally reflective mode.

4. The video inspection system of claim 2 wherein the light source is fabricated using solid-state light emitting elements.

5. The video inspection system of claim 4 wherein the solid-state light source is operated in a continuous forward current mode.

6. The video inspection system of claim 5 wherein the system is used to inspect manufactured food or beverage containers.

7. The video inspection system of claim 5 wherein the system is used to inspect manufactured durable goods.

8. The video inspection system of claim 5 wherein the camera is electronically strobed to stop the action of a dynamic subject.

9. The video inspection system of claim 8 wherein the system is used to inspect manufactured food or beverage containers.

10. The video inspection system of claim 8 wherein the system is used to inspect manufactured durable goods.

11. The video inspection system of claim 4 wherein the solid-state light source is operated in a pulsed current mode.

12. The video inspection system of claim 11 wherein the system is used to inspect manufactured food or beverage containers.

13. The video inspection system of claim 11 wherein the system is used to inspect manufactured durable goods.

14. The video inspection system as set forth in claim 1 wherein the field lens component operates in one of a generally transmissive mode and a generally reflective mode.

15. The video inspection system as set forth in claim 1 wherein the light source is fabricated using solid-state emitting elements.

16. The video inspection system of claim 15 wherein the solid-state light source is operated in a continuous forward current mode.

17. The video inspection system of claim 16 wherein the video inspection system is used to inspection manufactured food or beverage containers.

18. The video inspection system of claim 16 wherein the video inspection system is used to inspect manufactured durable goods.

19. The video inspection system of claim 16 wherein the camera is electrically strobed to stop the action of a dynamic subject.

20. The video inspection system of claim 19 wherein the system is used to inspect manufactured food or beverage containers.

21. The video inspection system of claim 19 wherein the system is used to inspect manufactured durable goods.

22. The video inspection system of claim 15 wherein the solid-state light source is operated in a pulsed current mode.

23. The video inspection system of claim 22 wherein the system is used to inspection manufactured food or beverage cans.

24. The video inspection system of claim 22 wherein the system is used to inspect manufactured durable goods.

25. The system as set forth in claim 1 wherein the selected regions are annular.

26. A video inspection system comprising:

a light source for generating light;

a field lens for
   receiving a portion of the light emitted by the light source,
   communicating the light portion to an object under inspection,
   receiving the light portion after the light portion has reflected off the object under inspection, and
   selectively re-directing light rays which have reflected off of the object under inspection in a manner which results in a non-linear magnification of selected application specific regions of interest on the object; and, an imaging lens/camera assembly adapted to receive light rays representing a modified image of the object under inspection, the modified image having the selected application specific regions of interest magnified in a non-linear manner, wherein the field lens is disposed between the object under inspection and the imaging lens/camera assembly.

27. The video inspection system as set forth in claim 26 further comprising:

a processor;

means for communicating digitized picture information from the camera to the processor;

the processor including means for determining acceptability of the item under inspection from the digitized picture information; and, means for selectively rejecting an associated specimen in accordance with acceptability of the object under inspection as determined by the processor.

28. The system as set forth in claim 26 wherein the selected regions are annular.

29. A video inspection system comprising:

a light source for generating light;

a field lens for
   receiving a portion of the light emitted by the light source,
   communicating the light portion to an object under inspection,
   receiving the light portion after the light portion has reflected off the object under inspection, and
   selectively re-directing light rays which have reflected off of the object under inspection in a manner which results in a magnification of selected regions of interest on the object to obtain a more advantageous look angle; and, an imaging lens/camera assembly adapted to receive light rays representing a modified image of the object under inspection, the modified image having the selected regions of interest presented with the more advantageous look angle, wherein the field lens is disposed between the object under inspection and the imaging lens/camera assembly.

30. The video inspection system as set forth in claim 29 further comprising:

a processor;

means for communicating digitized picture information from the camera to the processor;

the processor including means for determining acceptability of the item under inspection from the digitized picture information; and, means for selectively rejecting an associated specimen in accordance with acceptability of the object under inspection as determined by the processor.

31. The system as set forth in claim 29 wherein the selected regions are annular.

32. A video inspection method comprising the steps of:

generating light from a light source;

communicating generated light to an object under inspection;

after reflection from the object under inspection, selectively redirecting a portion of the light through a field lens in a non-linear manner to an imaging lens/camera assembly to magnify a selected region of the object to obtain a non-linear magnification thereof; and, receiving the redirected portion and mapping modified radiation fields representing the redirected portion onto a surface of a spatial light recording medium.

33. The video inspection methods of claim 32 further comprising the steps of:

digitizing the signal present on the surface of the spatial light recording medium;

communicating the digitized signal to a processing element;

determining acceptability of the object under inspection from information contained within the digitized signal; and, selectively rejecting an associated specimen in accordance with acceptability criteria as determined by the processing element.

34. The system as set forth in claim 32 wherein the selected region is annular.

* * * * *